(12) United States Patent
Erickson

(10) Patent No.: US 9,463,172 B2
(45) Date of Patent: Oct. 11, 2016

(54) MATERIAL AND METHODS FOR TREATING DEVELOPMENTAL DISORDERS INCLUDING COMORBID AND IDIOPATHIC AUTISM

(75) Inventor: Craig A. Erickson, Indianapolis, IN (US)

(73) Assignee: Indiana University Research & Technology Corporation, Indianapolis, IN (US)

(*) Notice: Subject to any disclaimer, the term of this patent is extended or adjusted under 35 U.S.C. 154(b) by 1282 days.

(21) Appl. No.: 13/201,014

(22) PCT Filed: Feb. 12, 2010

(86) PCT No.: PCT/US2010/024008
§ 371 (c)(1), (2), (4) Date: Aug. 11, 2011

(87) PCT Pub. No.: WO2010/093859
PCT Pub. Date: Aug. 19, 2010

(65) Prior Publication Data
US 2012/0016036 A1    Jan. 19, 2012

Related U.S. Application Data

(60) Provisional application No. 61/151,858, filed on Feb. 12, 2009.

(51) Int. Cl.
- *A61K 31/16* (2006.01)
- *A61K 31/185* (2006.01)
- *A61K 31/4035* (2006.01)

(52) U.S. Cl.
CPC ......... *A61K 31/185* (2013.01); *A61K 31/4035* (2013.01)

(58) Field of Classification Search
CPC .................. A61K 31/185; A61K 31/4035
See application file for complete search history.

(56) References Cited

U.S. PATENT DOCUMENTS

| 6,890,931 B2 | 5/2005 | Bear |
| 7,498,361 B2 | 3/2009 | Fogel |

(Continued)

FOREIGN PATENT DOCUMENTS

| WO | WO 00/56301 | 9/2000 |
| WO | WO 02/102388 | 12/2002 |

(Continued)

OTHER PUBLICATIONS

Gatchel et al (Nature Reviews | Genetics vol. 6 | Oct. 2005).*

(Continued)

*Primary Examiner* — Savitha Rao
*Assistant Examiner* — Angela Brown-Pettigrew
(74) *Attorney, Agent, or Firm* — Faegre Baker Daniels, LLP

(57) ABSTRACT

The present invention is directed to a method of treating a subject with autism spectrum disorder by administering an acetylaminopropane sulfonate. The acetylaminopropane sulfonate may have the following formula

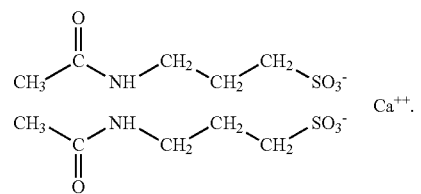

27 Claims, 1 Drawing Sheet

TABLE 1: Clinical demographics and treatment response data for 3 adult patients with fragile X syndrome (FXS)

| Patient no. | Diagnosis | Age (years) | Target Symptoms | Acamprosate dose (mg/day) | Duration of Treatment (weeks) | Concomitant Psychotropic Drugs | Treatment Response (CGI-I) | Adverse Effects |
|---|---|---|---|---|---|---|---|---|
| A | FXS, autism, mild intellectual disability | 20.8 | Aggression, social impairment, communication impairment | 1998 | 20 | Dexedrine, propranolol, ziprasidone | 1 | None |
| B | FXS, autism, moderate intellectual disability | 18 | Social impairment, communication impairment | 1332 | 20 | Aripiprazole | 1 | Emesis, nausea |
| C | FXS, autism, moderate intellectual disability | 23.9 | Social impairment, repetitive behavior | 333 | 16 | None | 2 | Emesis, sedation |

(56) References Cited

U.S. PATENT DOCUMENTS

| | | |
|---|---|---|
| 2004/0102525 A1 | 5/2004 | Kozachuk |
| 2005/0171067 A1 | 8/2005 | Bear |
| 2010/0317715 A1 | 12/2010 | Vollrath |

FOREIGN PATENT DOCUMENTS

| | | |
|---|---|---|
| WO | WO 2006/108055 | 10/2006 |
| WO | WO 2008/066750 | 6/2008 |
| WO | WO 2008/086483 | 7/2008 |

OTHER PUBLICATIONS

Reilly, M.T., Effects of Acamprosate on Neuronal Receptors and Ion Channels Expressed in Xenopus Oocytes, Alcohol Clin. Exp. Res., Feb. 2008, pp. 188-196 [pp. 1-18], vol. 32, No. 2.

De Witte Philippe et al: "Neuroprotective and abstinence-promoting effects of acamprosate: elucidating the mechanism of action." CNS Drugs vol. 19, No. 6, 2005, pp. 517-537.

Harris Barton R. et al: "Acamprosate inhibits the binding and neurotoxic effects of trans-ACPD, suggesting a novel site of action at metabotropic glutamate receptors." Alcoholism, Clinical and Experimental Research vol. 26, No. 12, Dec. 2002, pp. 1779-1793.

Littleton, John: Alcoholism Clinical and Experimental Research, vol. 29, No. 5, Suppl. S, May 2005, p. 173A, 28th Annual Meeting of the Research-Society-On-Alcoholism; Santa Barbara, CA, USA; June 25-30, 2005.

Gupta et al: "Taurine analogues: a new class of therapeutics: retrospect and prospects" Current Medicinal Chemistry, vol. 12, Jan. 2005, pp. 2021-2039.

Craig A Ericson et al: "Brief Report: Acamprosate in Fragile X Syndrome" Journal of Autism and Developmental Disorders, Mar. 2010 p. 5PP.

Dissanayake, Cheryl et al: "Behavorial and Cognitive Phenotypes in Idiopathic Autism versus Autism Associated with Fragile X Syndrome", Journal of Child Psychology and Psychiatry, vol. 50 No. 3, pp. 290-299. Mar. 2009.

International Search Report for PCT/U2010/024008, issued Apr. 2010.

The Written Opinion of the International Searching Authority for PCT/U2010/024008, issued Apr. 2010.

The International Preliminary Report on Patentability of the International Searching Authority for PCT/U2010/024008, issued Aug. 2011.

The Written Opinion of the International Searching Authority for PCT/U2010/024008, issued Aug. 2011.

\* cited by examiner

TABLE 1: Clinical demographics and treatment response data for 3 adult patients with fragile X syndrome (FXS)

| Patient no. | Diagnosis | Age (years) | Target Symptoms | Acamprosate dose (mg/day) | Duration of Treatment (weeks) | Concomitant Psychotropic Drugs | Treatment Response (CGI-I) | Adverse Effects |
|---|---|---|---|---|---|---|---|---|
| A | FXS, autism, mild intellectual disability | 20.8 | Aggression, social impairment, communication impairment | 1998 | 20 | Dexedrine, propranolol, ziprasidone | 1 | None |
| B | FXS, autism, moderate intellectual disability | 18 | Social impairment, communication impairment | 1332 | 20 | Aripiprazole | 1 | Emesis, nausea |
| C | FXS, autism, moderate intellectual disability | 23.9 | Social impairment, repetitive behavior | 333 | 16 | None | 2 | Emesis, sedation |

MATERIAL AND METHODS FOR TREATING DEVELOPMENTAL DISORDERS INCLUDING COMORBID AND IDIOPATHIC AUTISM

CROSS-REFERENCE TO RELATED APPLICATION

This application is a National Stage filing of International Application Serial No. PCT/US2010/024008, entitled "Materials and Methods for Treating Developmental Disorders Comorbid and Idiopathic Autism filed Feb. 12, 2010, which claims the benefit under 35 U.S.C. §119 of U.S. Provisional Application No. 61/151,858, filed Feb. 12, 2009, the disclosures of which are expressly incorporated herein by reference.

FIELD OF THE INVENTION

Various aspects related to drug therapy for the treatment of individuals with developmental disorders, such as autism and the genetic disorder Fragile X Syndrome.

BACKGROUND

Autism Spectrum Disorders (ASDs) are defined by the National Human Genome Research Institute as a broad group of developmental disorders characterized by impaired social interactions, problems with verbal and nonverbal communication and respective behaviors or severely limited activates and interests. Various forms of autism are included in the Diagnostic and Statistical manual of Mental Disorders DSM-IV-TR currently in its forth revised edition and listed as two of five known categories of pervasive developmental disorder. ASDs range from a severe form of the disorder called autistic disorder (or classic autism) to a milder form called Asperger's Disorder. A patient presenting symptoms of either of these disorders, but not meeting the specific criteria for either form, may be said to have pervasive developmental disorder not otherwise specified (PDD-NOS).

According to the National Institute for Mental Health an actual diagnosis of autism requires a thorough clinical examination by a physician trained in this area of medicine or even a team of health care professionals. An individual diagnosis is based on observing an individual patient's behaviors and measuring the patient's behavior using such screening tools such as Autism Diagnosis Interview-Revised (ADI-R) and the Autism Diagnostic Observation Schedule (ADOS). Comorbid autism such as autism co-diagnosed with conditions such as Down Syndrome or Fragile X Syndrome (FXS) comprise about 15 percent of all forms of autism, the remaining 85 percent of cases is of unknown origin and classified as idiopathic autism.

Given the profound effects that the most severe forms of autism spectrum disorders, including comorbid and idiopathic forms of the disorder, have on people afflicted with these disorders and the lack of effective treatment options available for these people there is pressing need for materials and methods to treat these patients, various aspects and embodiments presented herein seek to address this need.

SUMMARY

The invention generally relates to methods of treating fragile X syndrome and autism.

In an embodiment, the invention is a method of treating a subject having an autism spectrum disorder, comprising the step of administering to the subject a composition that includes at least one homotaurine analog.

In another embodiment, the invention is a method of treating a subject having fragile X syndrome, comprising the step of administering to the subject a composition that includes at least one homotaurine analog.

In a further embodiment, the invention is a method of treating a human having fragile X syndrome, comprising the step of administering to the human a composition that includes Formula I, wherein the composition is administered to the subject in a dose of about 333 mg at a frequency of at least one member selected from the group consisting of two times a day and three times a day.

In still another embodiment, the invention is a method of treating a human having an autism spectrum disorder, comprising the step of administering to the human a composition that includes Formula I, wherein the composition is administered to the subject in a dose of about 333 mg at a frequency of at least one member selected from the group consisting of two times a day and three times a day.

In still another embodiment, the invention is a method of treating a human having an autism spectrum disorder, comprising the step of administering to the human a composition that includes Formula I, wherein the composition is administered to the subject in a dose of at least about 333 mg at a frequency of at least one member selected from the group consisting of one time a day, two times a day and three times a day.

In still another embodiment, the invention is a method of treating a human having an autism spectrum disorder, comprising the step of administering to the human a composition that includes Formula I, wherein the composition is administered to the subject in a dose that is therapeutically effective.

BRIEF DESCRIPTION OF THE FIGURES

FIG. 1. Table 1.

DESCRIPTION

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates.

In an embodiment, the invention is a method of treating a subject having an autism spectrum disorder, comprising the step of administering to the subject a composition that includes at least one homotaurine analog that decreases neuronal glutamatergic signaling.

In another embodiment, the invention is a method of treating a subject having an autism spectrum disorder, comprising the step of administering to the subject a composition that includes at least one homotaurine analog. The homotaurine analog employed in the methods of the invention are homotaurine analogs that can decrease neuronal glutamatergic signaling.

Autism spectrum disorder is a developmental disorder that affects an individual's ability to communicate, form relationships with others and respond appropriately to the environment. Some individuals with autism spectrum disorder are high functioning, with speech and intelligence within normal range. Other individuals with autism spectrum disorder may be nonverbal and/or have varying degrees of mental retardation. Autism spectrum disorder can include Asperger's syndrome (also referred to as "Asperger's disorder"), idiopathic autism (e.g., autism of unknown origin) and Pervasive Developmental Disorder Not Otherwise Specified (PDD-NOS). One of skill in the art would be able to diagnose an individual with autism spectrum disorder and determine whether the individual has idiopathic autism, PDD-NOS or Asperger's syndrome, employing well-known clinical criteria as described, for example, in Diagnostic and Statistical Manual of Mental Disorders (DSMMD) (4th ed., pp. 70-71) Washington, D.C., American Psychiatric, 1994. Exemplary diagnostic criteria listed in the DSMMD include:

Autistic Disorder

An autism screening tool must meet all three primary areas defined by the DSM-IV description for autistic disorder (#'s 1-3 under A below) to qualify for a positive rating from First Signs:

A. A total of six (or more) items from (1), (2), and (3), with at least two from (1), and one each from (2) and (3):

(1) qualitative impairment in social interaction, as manifested by at least two of the following:

(a) marked impairment in the use of multiple nonverbal behaviors, such as eye-to-eye gaze, facial expression, body postures, and gestures to regulate social interaction (b) failure to develop peer relationships appropriate to developmental level (c) a lack of spontaneous seeking to share enjoyment, interests, or achievements with other people (e.g., by a lack of showing, bringing, or pointing out objects of interest)

(d) lack of social or emotional reciprocity (2) qualitative impairments in communication, as manifested by at least one of the following:

(a) delay in, or total lack of, the development of spoken language (not accompanied by an attempt to compensate through alternative modes of communication such as gesture or mime)

(b) in individuals with adequate speech, marked impairment in the ability to initiate or sustain a conversation with others (c) stereotyped and repetitive use of language or idiosyncratic language (d) lack of varied, spontaneous make-believe play or social imitative play appropriate to developmental level (3) restricted, repetitive, and stereotyped patterns of behavior, interests, and activities as manifested by at least one of the following:

(a) encompassing preoccupation with one or more stereotyped and restricted patterns of interest that is abnormal either in intensity or focus (b) apparently inflexible adherence to specific, nonfunctional routines or rituals (c) stereotyped and repetitive motor mannerisms (e.g., hand or finger flapping or twisting or complex whole-body movements)

(d) persistent preoccupation with parts of objects

B. Delays or abnormal functioning in at least one of the following areas, with onset prior to age 3 years: (1) social interaction, (2) language as used in social communication, or (3) symbolic or imaginative play.

C. The disturbance is not better accounted for by Rett's disorder or childhood disintegrative disorder.

Pervasive Developmental Disorder, Not Otherwise Specified (PDD-NOS)

Pervasive Developmental Disorder, Not Otherwise Specified (PDD-NOS) is a diagnosis often considered for children who show some signs of autism spectrum disorder, but who do not meet the specific diagnostic criteria for other Pervasive Developmental Disorders (PDDs) (see, for example, Diagnostic and Statistical Manual of Mental Disorders (4th ed., pp. 70-71) Washington, D.C., American Psychiatric, 1994). Deficits in peer relations and unusual sensitivities are generally observed in individuals with PDD-NOS, whereas social skills are generally less impaired than in idiopathic autism.

This category should be used when there is a severe and pervasive impairment in the development of reciprocal social interaction or verbal and nonverbal communication skills, or when stereotyped behavior, interests, and activities are present, but the criteria are not met for a specific pervasive developmental disorder, schizophrenia, schizotypal personality disorder, or avoidant personality disorder. For example, this category includes "atypical autism"—presentations that do not meet the criteria for autistic disorder because of late age of onset, atypical symptomatology, or subthreshold symptomatology, or all or any combination thereof.

Asperger's Disorder (also referred to herein as "Asperger Syndrome")

In contrast to individuals with idiopathic autism (autism with unknown origin) individuals with Asperger's syndrome generally do not manifest a delay in spoken language development (see, for example, Diagnostic and Statistical Manual of Mental Disorders (4th ed., pp. 70-71) Washington, D.C., American Psychiatric, 1994). However, they can have serious deficits in social and communication skills; and often have obsessive, repetitive routines and preoccupations with a particular subject matter. Idiosyncratic interests are common and may take the form of an unusual and/or highly circumscribed interest (e.g., in train schedules, the weather).

An Asperger/HFA screening tool must meet all six areas defined by the DSM-IV description of Asperger Syndrome (A-F below) to qualify for a positive rating from First Signs:

A. Qualitative impairment in social interaction, as manifested by at least two of the following:

(1) marked impairment in the use of multiple nonverbal behaviors, such as eye-to-eye gaze, facial expression, body postures, and gestures to regulate social interaction (2) failure to develop peer relationships appropriate to developmental level (3) a lack of spontaneous seeking to share enjoyment, interests, or achievements with other people (e.g., by a lack of showing, bringing, or pointing out objects of interest to other people)

(4) lack of social or emotional reciprocity

B. Restricted, repetitive, and stereotyped patterns of behavior, interests, and activities, as manifested by at least one of the following:

(1) encompassing preoccupation with one or more stereotyped and restricted patterns of interest that is abnormal either in intensity or focus (2) apparently inflexible adherence to specific, nonfunctional routines or rituals (3) stereotyped and repetitive motor mannerisms (e.g., hand or finger flapping or twisting, or complex whole-body movements)

(4) persistent preoccupation with parts of objects

C. The disturbance causes clinically significant impairment in social, occupational, or other important areas of functioning.

D. There is no clinically significant general delay in language (e.g., single words used by age 2 years, communicative phrases used by age 3 years).

E. There is no clinically significant delay in cognitive development or in the development of age-appropriate self-help skills, adaptive behavior (other than in social interaction), and curiosity about the environment in childhood.

F. Criteria are not met for another specific pervasive developmental disorder or schizophrenia.

"Homotaurine analog," as used herein, means a compound that has a structure that is similar to taurine but differs by at least one element. For example, taltrimide (Formula II), calcium acamprosate (Formula I) and tauromustine (Formula III) are homotaurine analogs (Gupta, R. C., et al., Curr. Medicinal Chem. 12:2021-2039 (2005)).

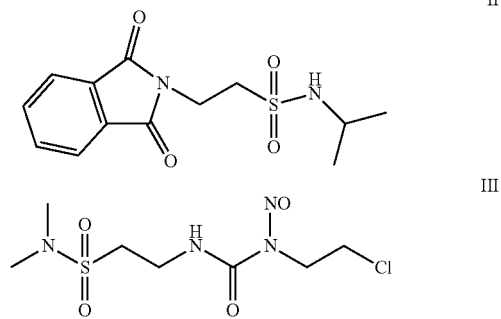

The methods of the invention employ homotaurine analogs (See, for example, U.S. Pat. Nos. 6,391,922 and 5,602,150, each of which is incorporated herein in its entirety; U.S. Patent Application Nos.: 2002/0013366, 2002/0119912, 2004/0102525, each of which is incorporated herein in its entirety; Harris, B. R., et al., Alcohol Clin Exp Res 26: 1779-1793 (2002); and Pierrefiche, O., et al., Neuropharmacology 47:35-45 (2004)).

The methods of the invention employ the homotaurine analog of Formula I:

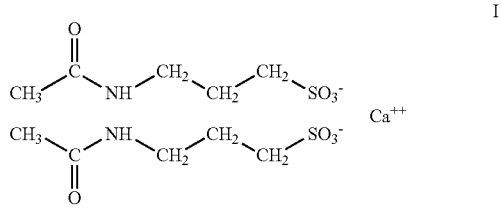

The chemical name of Formula I is calcium acetylaminopropane sulfonate, calcium bis-acetyl homotaurine or calcium N-acetylhomotaurine. The chemical formula for Formula I is C10H20N2O8S2Ca. Formula I is referred to as CAMPRAL® (acamprosate calcium, also referred to herein as "calcium acamprosate"). Formula I decreases neuronal glutamateric signaling.

"Decreases neuronal glutamatergic signaling," as used herein, means that the homotaurine analog reduces the amount of effect of glutamate on postsynaptic transmission in neurons. A decrease in neuronal glutamatergic signaling can be, for example, consequent to a decrease in release of glutamate from neurons and/or limiting or diminishing the ability of synaptic glutamate to mediate cell signaling in neurons. Techniques to assess whether a homotaurine analog can decrease neuronal glutamateric signaling are well established and known to one of skill in the art and include, for example, the use of paired pulse facilitation to measure glutamate release using electrophysiologic measure, as described, for example, by MacIver, M., et al., Laboratory Investigation 85 (Issue 4), pp 823-834 (1996).

The autism spectrum disorder treated by the methods of the invention can include at least one member selected from the group consisting of Asperger's syndrome, an idiopathic autism and a pervasive developmental disorder not otherwise specified (PDD-NOS).

In an embodiment, the subject that has autism spectrum disorder also has fragile X syndrome.

The homotaurine analog employed in the methods of the invention to treat an autism spectrum disorder (Asperger's syndrome, idiopathic autism, PDD-NOS) and/or fragile X syndrome can include at least one member selected from the group consisting of an acetylaminopropane sulfonate and an acetylaminopropane sulfonate salt. In a particular embodiment, the acetylaminopropane sulfonate salt can include a calcium acetylaminopropane sulfonate represented by Formula I:

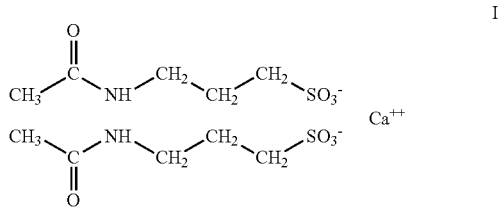

The homotaurine analog employed in some of the methods of the invention (e.g., calcium acetylaminopropane sulfonate, Formula I) can be administered to the subject at a dose of at least one member selected from the group consisting of about a 333 mg dose, about a 666 mg dose, about a 999 mg dose, about a 1332 mg dose, about a 1665 mg dose, about a 1998 mg dose, about a 2331 mg dose, about a 2664 mg dose and about a 2997 mg dose. The homotaurine analog (e.g., Formula I) employed in the methods of the invention can be administered to the subject in a dose of about 1221 mg/day or in a dose of between about 333 mg/day to about 1999 mg/day. In an embodiment, the subject is administered a dose of the homotaurine analog (e.g., Formula I) of about a 333 mg dose. In another embodiment, the subject is administered a dose of the homotaurine analog (e.g., Formula I) of about a 666 mg dose.

The homotaurine analogs (e.g., Formula I) can be administered to the subject (e.g., a human subject) daily in a single dose or in multiple doses (e.g., two doses, three doses, four doses, five doses, six doses, seven doses, eight doses, nine doses, ten doses) a day. The dosage and frequency of dosing of the subject can within the knowledge of one of skill in the art based on age, other medications and tolerance of the homotaurine analog.

In another embodiment, the invention is a method of treating a subject having fragile X syndrome, comprising the step of administering to the subject a composition that includes at least one homotaurine analog. The homotaurine analog employed to treat the subject having fragile x syndrome, autism or a combination of autism and fragile X syndrome can decrease neuronal glutamatergic signaling. The subject having fragile X syndrome treated by the methods of the invention can also further have an autism spectrum disorder.

In yet another embodiment, the invention is a method of treating a human having fragile X syndrome, comprising the step of administering to the human a composition that includes Formula I, wherein the composition is administered to the subject in a dose of about 333 mg at a frequency of at least one member selected from the group consisting of two times a day and three times a day. The human treated with Formula I that has fragile X syndrome can further have an autism spectrum disorder.

In still another embodiment, the invention is a method of treating a human having an autism spectrum disorder, comprising the step of administering to the human a composition that includes Formula I, wherein the composition is administered to the subject in a dose of about 333 mg at a frequency of at least one member selected from the group consisting of two times a day and three times a day. The human that has autism spectrum disorder that is treated by administering Formula I can further have fragile X syndrome.

"Therapeutically effective amount," as used herein, means an amount of a homotaurine analog that diminishes or ameliorates symptoms of at least one condition selected from the group consisting of an autism spectrum disorder and fragile X syndrome. One of skill in the art would be able to determine the therapeutically effective amount of a homotaurine analog for use in the methods described herein.

The methods of the invention can further include the step of administering compositions to the subject that treat irritability, anxiety, inattention and hyperactivity in the subjects, as needed (referred to as "additional treatment"). The additional treatment could be administered before or after administration of the homotaurine analog to the subject. Suitable compositions for administration to the subject in addition to the homotaurine analog can include, for example, aripiprazole and risperidone in subject having autism; selective serotonin reuptake inhibitors (SSRIs) to treat anxiety and stimulants to treat ADHD-like symptoms in subjects with fragile X syndrome; stimulants, alpha 2-agonists and atomoxetine to manage ADHD-like symptoms and SSRIs; and mirtazapine for anxiety in subjects with idiopathic autism. One of skill in the art would be able to identify subjects who need additional treatment and the additional treatment that is required.

FXS represents the most common known cause of autism and related disorders. Approximately 1 in 4 (25%) to 1 in 3 (33%) individuals with FXS additionally meet criteria for autistic disorder (King, State et al. 1997; Bailey, Hatton et al. 2001; Rogers, Wehner et al. 2001). About 2 in 3 (67%) males with FXS are thought to exhibit behavior consistent with the broader autism phenotype (Clifford, Dissanayake et al. 2007).

Experiments utilizing cellular and animal modeling, in recent years have contributed to our understanding of the possible etiology of FXS. Some of this work has reported that excessive metabotropic glutamate receptor activation (specifically mGluR5 activation) may be involved in the pathogenesis of FXS (Bear, Huber et al. 2004; Bear 2005; Dolen and Bear 2005; Dolen, Osterweil et al. 2007; Bear, Dolen et al. 2008; Dolen and Bear 2008). In some experiments, the mGluR5 antagonist MPEP (2-methyl-6-phenylethynyl)-pyridine) has demonstrated its apparent ability to reverse aspects of the FXS phenotype in animal models for the syndrome (McBride, Choi et al. 2005; Yan, Rammal et al. 2005; Tucker, Richards et al. 2006; Dolen, Osterweil et al. 2007).

Fragile X syndrome (FXS) is the most common inherited form of intellectual disability. FXS is the result of an unstable cysteine-guanine-guanine (CGG) trinucleotide repeat expansion (>200 repeats) within the fragile X mental retardation 1 gene (FMR1) promoter region located near the long arm of the X chromosome (Pieretti, Zhang et al. 1991). This expansion leads to transcriptional silencing of the FMR1 gene and the absence of fragile X mental retardation protein (FMRP) (Devys, Lutz et al. 1993). Due to the location of the FMR1 gene on the X chromosome, females with the full mutation are, in general, more mildly affected than males secondary to potential FMRP production from the non-mutated FMR1 allele. The full mutation gene frequency is about 1/2500 (Hagerman 2008).

FMRP is an RNA binding protein important to dendritic maturity and synaptic plasticity (Greenough, Klintsova et al. 2001). This important role in cortical development is likely in part due to the action of FMRP as an end product inhibitor of group 1 metabotropic glutamate receptor (mGluR1 and mGluR5) mediated dendritic RNA translation (Bear, Huber et al. 2004; Ronesi and Huber 2008). The impact of excess mGluR activation due to loss of inhibitory FMRP control can be seen in the FMR1 knockout mouse model. In this model, excess hippocampal and cerebellar long term depression (LTD), excess AMPA receptor internalization, abnormal dendritic morphology, and reduced seizure threshold are all consistent with excessive group 1 mGluR activation (Bear, Huber et al. 2004).

Some of the treatment implications of excessive mGluR activation have been studied. In the mouse model, mGluR down regulation by treatment with MPEP (2-methyl-6-(phenylethynyl)-pyridine) and other mGluR5 antagonists has been shown to reverse phenotypic characteristics, including audiogenic seizures, altered prepulse inhibition (PPI), and open field hyperactivity (Chuang, Zhao et al. 2005; Yan, Rammal et al. 2005; de Vrij, Levenga et al. 2008). MPEP has rescued aberrant courtship behavior in the Drosophila model of FXS (McBride, Choi et al. 2005). Genetic down regulation of mGluR5 executed by crossing a FMR1 knockout mouse with a mGluR5 heterozygous knockout resulted in reversal of several FMR1 knockout characteristics, including dendritic spine changes and excess protein synthesis (Dolen and Bear 2008).

Berry-Kravis and colleagues (2008) conducted a pilot single dose trial of the mGluR5 antagonist fenobam (50-150 mg) focused on tolerability and pharmacokinetic assessment in twelve adults (6 males, 6 females; mean age, 23.9+/−5.4 years) with full mutation FXS (Berry-Kravis, Hessl et al. 2009). Fenobam was generally well tolerated with only 3 (25%) subjects exhibiting mild sedation. Wide inter-subject pharmacokinetic variability was noted. Six (50%) subjects showed at least a 20% improvement in PPI one hour post fenobam dosing. The authors reported that nine (75%) subjects experienced clinical benefit, including reduced hyperactivity and anxiety that was not dose dependent and did not completely correlate with PPI response.

Acamprosate, calcium acetylhomotaurine, also known as 3-acetamidopropane-1-sulfonic acid, is approved by the United States Food and Drug Administration to administer to patients for the maintenance of abstinence from alcohol in patients with alcohol dependence. See for example, International Publication Number WO 02/102388 A3, incorporated by reference herein in its entirety.

Recent research into the mechanism of action of acamprosate has focused on mGluR5 antagonism (Harris, Prendergast et al. 2002; Blednov and Adron Harris 2008; Gupta, Syed et al. 2008). In rat brain specimens, Harris et al. (2002) initially demonstrated that acamprosate had binding and functional characteristics consistent with an mGluR antagonist combined with functional similarity to the non-competitive mGluR5 antagonist SIB-1893 (Harris, Prendergast et al. 2002). Acamprosate and MPEP have both been associated with increased sedative effects of alcohol and reduced alcohol withdrawal in mice; no effects of acamprosate or MPEP were noted in mGluR5 knockout mice (Blednov and Adron Harris 2008). Gupta and colleagues (2008) demonstrated that acamprosate and MPEP both dose dependently reduced ethanol drinking in the drinking-in-the-dark mouse model (Gupta, Syed et al. 2008). In a conflicting report, at concentrations typically achieved in humans, acamprosate did not modulate the function of many neuroreceptors, including mGluR receptors, in an electrophysiological study in *Xenopus oocytes* (Reilly, Lobo et al. 2008). Additional preclinical data has pointed to potential weak NMDA receptor antagonism, GABA(A) receptor agonism, and anti-oxidant effects as potentially contributing to the effect of the drug in early alcohol abstinence (Mann, Kiefer et al. 2008).

In this report, no effects of acamprosate or MPEP were noted in mGluR5 knockout mice (Blednov and Adron Harris 2008). Also recently, Gupta et al. (2008) demonstrated that both acamprosate and MPEP dose dependently reduced ethanol drinking in the drinking-in-the-dark mouse model (Gupta, Syed et al. 2008). And MPEP, itself, has been shown to possibly reverse some aspects of the FXS phenotype in several animal models for the condition.

According to current FDA guidelines acamprosate can be administered to human patients at a dosing level of about 1,998 mg/kg/day which is the U.S. FDA approved dosing of acamprosate used to treat alcohol dependence in adults. The calcium salt of the compound is commercially available and sold in tablets that include about 333 mg of the active ingredient per tablet. Tablets that have an enteric coating are also available to administer to patents that are able to swallow tablets.

In some embodiments patients already being treated with psychotropic drug use will be allowed to continue to use these drugs throughout the study as long as the dose of psychotropic drugs remains the same during the trial. Experimental primary outcome measures in the studies reported on herein and any ongoing studies and clinical assessments may include tests such as the Clinical Global Impression Improvement (CGI-I) scale (Guy 1976) and the Aberrant Behavior Checklist (ABC) (Aman, Singh et al. 1985). The ABC is made up of subscales of behaviors including Social Withdrawal, Irritability, Stereotypy, Hyperactivity, and Inappropriate Speech. The ABC is commonly used in drug trials involving persons with developmental disability and the composite score on the measure has shown good reliability as an outcome measure specifically in persons with FXS (Berry-Kravis, Krause et al. 2006). Treatment responses using these tests are determined by scoring the behaviors of the patients' a CGI-I score of "much improved" or "very much improved" and a 25% or greater improvement in the ABC composite score. The tolerability of acamprosate can be readily assessed throughout the course of treatment with the drug via the use of standard side-effect profile checklists at all study visits and by the following baseline and study completion measures: physical examination; laboratory studies including complete blood count, comprehensive metabolic panel, and lipid panel; electrocardiograms.

EXPERIMENTAL

1. Treatment of Young Adult Males Presenting with Full Mutation FXS.

This study sample included 4 young adult males (mean age, 20.3 years; range, 18-23 years) with full mutation FXS. The parents of each patient gave their written, informed consent for treatment within our clinic. All patients had a comorbid clinical diagnosis of autistic disorder (autism) utilizing Diagnostic and Statistical Manual of Mental Disorders, $4^{th}$ Edition, Text Revision criteria (American Psychiatric Association 2000). Patients A and B had this diagnosis corroborated by the Autism Diagnostic Interview-Revised (ADI-R) (Lord, Rutter et al. 1994). At baseline, each patient had linguistic communication. Two patients (A, B) receiving concomitant psychotropic drugs were continued at the same doses during the trial (see Table 1).

Acamprosate was initiated at 666 mg every morning and increased in 666 mg increments every 2 weeks as tolerated to a maximum dose of 666 mg three times daily (recommended dose for treatment of alcohol-dependent adults) (Forest Pharmaceuticals 2005). Prior to reaching a maintenance dose, and in between monthly clinic visits, phone calls were made every two weeks to the primary caregiver to assess for treatment response and drug tolerability. Global improvement, as measured by the Clinical Global Impressions-Improvement (Guy 1976) (CGI-I) scale was assigned at the time of last follow-up visit. The CGI-I scale is rated from 1-7 (1=very much improved; 2=much improved; 3=minimally improved; 4=no change; 5=minimally worse; 6=much worse; 7=very much worse). The CGI-I ratings described change in target symptoms defined at the baseline visit (see Table 1). Patients were considered treatment responders if assigned a CGI-I score of 1 or 2 at the final follow-up visit. This study was approved by our local Institutional Review Board and, thus, has been performed in accordance with the ethical standards laid down in the 1964 Declaration of Helsinki.

Results

Case 1

A is a 20-year-old Caucasian male with mild intellectual disability. In addition to the characteristic features of autism (social impairment, communication impairment, repetitive phenomena), A had a history of significant physical aggression, anxiety, inattention, and hyperactivity. Previous trials of aripiprazole and risperidone were unsuccessful in limiting A's aggression. In addition to his current medication regimen, including propranolol, dextroamphetamine, and ziprasidone, a trial of acamprosate targeting aggression and social and communication impairments was initiated. Acamprosate was started at 666 mg every morning and increased to a target dose of 666 mg three times daily over 4 weeks. During the 44-week treatment, A exhibited increased communicative use of language marked by an expanded expressive vocabulary, increased grammatical complexity of speech, and improved pragmatic skills. For example, within 2 weeks of reaching his maximum dose, A reportedly started to appropriately initiate conversation with neighbors as they walked by his home while he was sitting on his front porch. A's increased mean length of utterance when responding to questions was clear at each follow-up visit. Additionally, A exhibited decreased physical aggression, use of foul language, and defiance during the acamprosate trial. He was deemed to be "very much improved" as determined by a CGI-I score of 1. No adverse effects were observed or reported.

Case 2

B is an 18-year-old Caucasian male with moderate intellectual disability. B had a history of intermittent physical aggression that was reduced significantly with aripiprazole. A trial of acamprosate targeting social skill deficits and communication impairment was begun. At baseline, B exhibited significantly impaired language pragmatics, grammatical complexity of speech, and expressive vocabulary. He would rarely use single words in social settings and only on occasion utilized short sentences with close family members at home Acamprosate was started at 666 mg every morning and increased to a target dose of 666 mg three times daily over 4 weeks. B experienced nausea and intermittent emesis requiring a dose reduction to 666 mg twice daily. During 40 weeks of acamprosate treatment, he utilized coherent full sentences in social settings for the first time, surprising family friends and peers. During follow-up visits, B's increased grammatical complexity of speech, expressive vocabulary, and pragmatic use of language were all evident. He was deemed to be "very much improved" as determined by a CGI-I score of 1.

Case 3

C is a 23-year-old Caucasian male with moderate intellectual disability. H is primary target symptoms were core symptoms of autism, including social skill deficits and repetitive behavior marked by repetitive questioning. C was unable to tolerate initial dosing of acamprosate monotherapy started at 666 mg every morning due to sedation and emesis. With a dose reduction to 333 mg daily, the sedation and emesis remitted and he continued the drug for 24 weeks. C's language pragmatics was described as improved, marked by an increased ability to convey his needs and interests in socially appropriate ways. He was described as asking more appropriate and not just repetitive questions, and generally "talking more on topic". He was deemed "much improved" as determined by a CGI-I score of 2.

Case 4

D is an 18-year-old Caucasian male with mild intellectual disability. His primary target symptoms were irritability and core symptoms of PDD-NOS including deficits of social communication. D was dosed up to 666 mg three times daily, but developed gastrointestinal upset on three times daily dosing. A dosing change to 999 mg twice daily was well tolerated for the duration of a total of 28 weeks of acamprosate treatment. D remained on stable concomitant dosing of aripiprazole, clonidine, and fluoxetine during treatment with acamprosate. During acamprosate treatment, D was described as exhibiting more appropriate use of sentences including use of an expanded vocabulary. D was generally more talkative during treatment. D exhibited reduced irritable behavior throughout acamprosate treatment. He was deemed "much improved" as determined by a CGI-I score of 2.

The mean final dose of acamprosate for the four young adult male FXS participants was 1415 mg/day (range, 333-1998 mg/day). Patients received the drug for a minimum of 24 weeks (mean duration, 34 weeks; range, 24-44 weeks). All 4 patients were deemed responders. Each subject exhibited positive expressive language change, including elements of improved pragmatics, grammatical complexity, and vocabulary. This increased linguistic communication was not associated with a reduction in gaze aversion or other forms of impaired non-verbal communication. One subject experienced sedation and two experienced nausea and/or emesis which appeared to be dose related.

2. Treatment of Juvenile Diagnosed with Full Mutation FXS.

In this study, acamprosate was initiated at 333 mg every morning and increased in 333 mg increments every 2 weeks as tolerated to a maximum dose of 666 mg three times daily (recommended dose for treatment of alcohol-dependent adults) (Forest Pharmaceuticals 2005). Prior to reaching a maintenance dose, and in between monthly clinic visits, phone calls were made every two weeks to the primary caregiver to assess for treatment response and drug tolerability. Drug dosing was held at a consistent level unless the patient exhibited untolerable side-effects from the therapy. Global improvement, as measured by the Clinical Global Impressions-Improvement (Guy 1976) (CGI-I) scale was assigned at the time of last follow-up visit. The CGI-I scale is rated from 1-7 (1=very much improved; 2=much improved; 3=minimally improved; 4=no change; 5=minimally worse; 6=much worse; 7=very much worse). The CGI-I ratings described change in target symptoms defined at the baseline visit (see Table 1). Patients were considered treatment responders if assigned a CGI-I score of 1 or 2 at the final follow-up visit.

Case 5

E is a 9-year-old Caucasian male with mild intellectual disability and full mutation FXS. His primary target symptoms include social use of language, inattention, hyperactivity, and general social relatedness. E has a comorbid diagnosis of PDD-NOS. E remained on a stable dose of concomitant aripiprazole throughout treatment with acamprosate. E was maintained on a starting dose of acamprosate at 333 mg every morning due to sufficient treatment response at this dose over 6 weeks of treatment. During treatment, E was described by his mother as seeming like "his brain has come back." E exhibited improved language pragmatics, improved focus, and remained calmer during use of acamprosate. He was deemed "very much improved" as determined by a CGI-I score of 1.

3. Treatment of Juveniles Diagnosed with Idiopathic Autism.

In this study, acamprosate was initiated at 333 mg every morning and increased in 333 mg increments every 2 weeks as tolerated to a maximum dose of 666 mg three times daily (recommended dose for treatment of alcohol-dependent adults) (Forest Pharmaceuticals 2005). Prior to reaching a maintenance dose, and in between monthly clinic visits, phone calls were made every two weeks to the primary caregiver to assess for treatment response and drug tolerability. Drug dosing was held at a consistent level unless the patient protested untolerable side-effects due to the therapy. Global improvement, as measured by the Clinical Global Impressions-Improvement (Guy 1976) (CGI-I) scale was assigned at the time of last follow-up visit. The CGI-I scale is rated from 1-7 (1=very much improved; 2=much improved; 3=minimally improved; 4=no change; 5=minimally worse; 6=much worse; 7=very much worse). The CGI-I ratings described change in target symptoms defined at the baseline visit (see Table 1). Patients were considered treatment responders if assigned a CGI-I score of 1 or 2 at the final follow-up visit. This study was approved by our local Institutional Review Board and, thus, has been performed in accordance with the ethical standards laid down in the 1964 Declaration of Helsinki.

Case 6

F is a 10-year-old male with idiopathic autistic disorder and mild intellectual disability. His primary target symptoms of treatment were social responsiveness and use of language. He received acamprosate treatment for 14 weeks with a final dosing of 666 mg in the morning, 333 mg midday, and 333 mg in the evening. F suffered from loose stools during acamprosate treatment. For F acamprosate treatment was associated with improved social responses, increased verbalizations, and improved eye contact. He was deemed "much improved" as determined by a CGI-I score of 2.

Case 7

G is a 13-year-old male with idiopathic autistic disorder and moderate intellectual disability. His primary target symptoms of treatment were social responsiveness and inattention. He received acamprosate treatment for 10 weeks with a final dosing of 333 mg twice daily. G remained on stable dosing of concomitant atomoxetine treatment throughout his acamprosate trial. For G acamprosate treatment was associated with improved attention and mildly improved social behavior. He was deemed "minimally improved" as determined by a CGI-I score of 3.

Case 8

H is a 12-year-old female with idiopathic autistic disorder and moderate intellectual disability. Her primary target symptoms of treatment were social responsiveness and use of language. She received acamprosate treatment for 28 weeks with a final dosing of 333 mg three times daily. She remained on stable dosing of concomitant risperidone and clonidine throughout her treatment with acamprosate. For H acamprosate treatment was associated with increased use of single words, generally improved social communication, and improved eye contact. She was deemed "very much improved" as determined by a CGI-I score of 1.

Case 9

I is an 11-year-old male with idiopathic autistic disorder and moderate intellectual disability. His primary target symptoms of treatment were social responsiveness and use of language. He received acamprosate treatment for 20 weeks with a final dosing of 333 mg three times daily. I remained on stable dosing of concomitant sertraline during his acamprosate trial. For I, acamprosate treatment was associated with initial improvement in social behavior that waned after 8-12 weeks of treatment. I additionally suffered from reduced appetite and gastrointestinal distress during treatment. He was described as "no change" as determined by a CGI-I score of 4.

Case 10

J is a 6-year-old male with idiopathic autistic disorder and severe intellectual disability. His primary target symptoms of treatment were social responsiveness, inattention, and use of language. He received acamprosate treatment for 20 weeks with a final dosing of 333 mg three times daily. For J acamprosate treatment was associated with improved following of directions, improved focus, and increased use of communication with gestures. J suffered from reduced appetite during acamprosate treatment. He was deemed "much improved" as determined by a CGI-I score of 2.

Case 11

K is an 8-year-old male with idiopathic autistic disorder and moderate intellectual disability. His primary target symptoms of treatment were social responsiveness, inattention, and use of language. He received acamprosate treatment for 30 weeks with a final dosing of 666 mg in the morning, 333 mg midday, and 333 mg in the evening. K suffered from reduced appetite and gastrointestinal distress that waned after several weeks of treatment with acamprosate. For K acamprosate treatment was associated with increased meaningful use of words, improved social relatedness, and improved focus. He was deemed "much improved" as determined by a CGI-I score of 2.

The six juveniles (mean age 10.3 years; range 6-13 years) with idiopathic autism were treated with a mean acamprosate dose of 999 mg/day over a mean 20.33 weeks of treatment.

All but one of the 11 patients treated with acamprosate calcium in this study showed a measurable improvement in standard assessments of functionality. Overall, use of acamprosate was associated with increased use of communicative language in all subjects. In all cases pragmatic language change was noted, as linguistic communication was more social in nature and the content more appropriate to the context of a given discussion. Despite improved pragmatics, nonverbal aspects of social communication including eye gaze, did not appear to change significantly. Acamprosate may enhance standard measures of expressive language, including assessment of mean length of utterance, vocabulary, and pragmatics of speech, along with systematic measures of interfering behaviors such as aggression.

The majority of both adult and juvenile human patients diagnosed with a form of autism spectrum disorder, show measurable improvement when treated with acamprosate. These clinical studies show that acamprosate can improve, for example, social behavior and use of language, resulting in a remarkable treatment for core symptoms of autism and/or fragile X syndrome, including communication and social impairments in these individuals. In addition to these remarkable and unexpected results still other advantages of using acamprosate to treat autism spectrum disorders include the commercial availability of the drug, limited drug-drug interactions given lack of hepatic metabolism, and demonstrated pharmacokinetic and safety profiles in human adults.

Additional potential properties of acamprosate, including mild NMDA receptor antagonism and GABA(A) agonism, could also be responsible for the treatment response noted. The possible contribution of these non-mGluR5 mediated treatment effects is supported by a report of modest treatment effects with use of the uncompetitive NMDA receptor antagonist memantine in an open-label study in 6 persons with FXS and a comorbid autism spectrum disorder (Erickson, Mullett et al. 2009).

REFERENCES

Aman, M. G., N. N. Singh, et al. (1985). "The Aberrant Behavior Checklist: a behavior rating scale for the assessment of treatment effects." *American Journal of Mental Deficiency* 5: 485-491.

American Psychiatric Association (2000). *Diagnostic and Statistical Manual of Mental Disorders, Four Edition, Text Revision*. Washington, D.C., American Psychiatric Association.

Bailey, D. B., Jr., D. D. Hatton, et al. (2001). "Autistic behavior, FMR1 protein, and developmental trajectories in young males with fragile X syndrome." *J Autism Dev Disord* 31(2): 165-74.

Bear, M. F. (2005). "Therapeutic implications of the mGluR theory of fragile X mental retardation." *Genes Brain Behav* 4(6): 393-8.

Bear, M. F., G. Dolen, et al. (2008). "Fragile X: translation in action." *Neuropsychopharmacology* 33(1): 84-7.

Bear, M. F., K. M. Huber, et al. (2004). "The mGluR theory of fragile X mental retardation." *Trends Neurosci* 27(7): 370-7.

Berry-Kravis, E., D. Hessl, et al. (2009). "A pilot open label, single dose trial of fenobam in adults with fragile X syndrome." *J Med Genet* 46(4): 266-71.

Berry-Kravis, E., S. E. Krause, et al. (2006). "Effect of CX516, an AMPA-modulating compound, on cognition and behavior in fragile X syndrome: a controlled trial." *J Child Adolesc Psychopharmacol* 16(5): 525-40.

Blednov, Y. A. and R. Adron Harris (2008). "Metabotropic glutamate receptor 5 (mGluR5) regulation of ethanol sedation, dependence and consumption: relationship to acamprosate actions." *Int J Neuropsychopharmacol* 11(6): 775-93.

Chuang, S. C., W. Zhao, et al. (2005). "Prolonged epileptiform discharges induced by altered group I metabotropic glutamate receptor-mediated synaptic responses in hippocampal slices of a fragile X mouse model." *J Neurosci* 25(35): 8048-55.

Clifford, S., C. Dissanayake, et al. (2007). "Autism spectrum phenotype in males and females with fragile X full mutation and premutation." *J Autism Dev Disord* 37(4): 738-47.

de Vrij, F. M., J. Levenga, et al. (2008). "Rescue of behavioral phenotype and neuronal protrusion morphology in Fmr1 KO mice." *Neurobiol Dis* 31(1): 127-32.

Devys, D., Y. Lutz, et al. (1993). "The FMR-1 protein is cytoplasmic, most abundant in neurons and appears normal in carriers of a fragile X premutation." *Nat Genet.* 4(4): 335-40.

Dolen, G. and M. F. Bear (2005). "Courting a cure for fragile X." *Neuron* 45(5): 642-4.

Dolen, G. and M. F. Bear (2008). "Role for metabotropic glutamate receptor 5 (mGluR5) in the pathogenesis of fragile X syndrome." *J Physiol* 586(6): 1503-8.

Dolen, G., E. Osterweil, et al. (2007). "Correction of fragile X syndrome in mice." *Neuron* 56(6): 955-62.

Erickson, C. A., J. E. Mullett, et al. (2009). "Open-Label Memantine in Fragile X Syndrome." *J Autism Dev Disord.*

Forest Pharmaceuticals, I. (2005). "Campral Product Information." Retrieved Aug. 17, 2009, from http://www.frx.com/pi/campral_pi.pdf.

Greenough, W. T., A. Y. Klintsova, et al. (2001). "Synaptic regulation of protein synthesis and the fragile X protein." *Proc Natl Acad Sci USA* 98(13): 7101-6.

Gupta, T., Y. M. Syed, et al. (2008). "Acute effects of acamprosate and MPEP on ethanol Drinking-in-the-Dark in male C57BL/6J mice." *Alcohol Clin Exp Res* 32(11): 1992-8.

Guy, W. (1976). ECDEU assessment manual for psychopharmacology, Publication No. 76-338. Washington, D.C., U.S. DHEW, NIMH.

Hagerman, P. J. (2008). "The fragile X prevalence paradox." *J Med Genet* 45(8): 498-9.

Hagerman, R., E. Berry-Kravis, et al. (2008). "Trial of fenobam, an mGluR5 antagonist, in adults with Fragile X Syndrome." *J Intellect Disabil Res* 52(10): 814.

Hagerman, R. J. (2006). "Lessons from fragile X regarding neurobiology, autism, and neurodegeneration." *J Dev Behav Pediatr* 27(1): 63-74.

Hagerman, R. J., M. Y. Ono, et al. (2005). "Recent advances in fragile X: a model for autism and neurodegeneration." *Curr Opin Psychiatry* 18(5): 490-6.

Harris, B. R., M. A. Prendergast, et al. (2002). "Acamprosate inhibits the binding and neurotoxic effects of trans-ACPD, suggesting a novel site of action at metabotropic glutamate receptors." *Alcohol Clin Exp Res* 26(12): 1779-93.

Jaeschke, G., J. G. Wettstein, et al. (2008). "mGlu5 receptor antagonists and their potential therapeutic potential." *Expert Opin Ther Patents* 18(2): 123-142.

King, B. H., M. W. State, et al. (1997). "Mental retardation: a review of the past 10 years. Part I." *J Am Acad Child Adolesc Psychiatry* 36(12): 1656-63.

Lombroso, P. J. and M. P. Ogren (2008). "Fragile X syndrome: keys to the molecular genetics of synaptic plasticity." *J Am Acad Child Adolesc Psychiatry* 47(7): 736-9.

Lord, C., M. Rutter, et al. (1994). "Autism Diagnostic Interview-Revised: a revised version of a diagnostic interview for caregivers of individuals with possible pervasive developmental disorders." *J Autism Dev Disord* 24(5): 659-85.

Mann, K., F. Kiefer, et al. (2008). "Acamprosate: recent findings and future research directions." *Alcohol Clin Exp Res* 32(7): 1105-10.

McBride, S. M., C. H. Choi, et al. (2005). "Pharmacological rescue of synaptic plasticity, courtship behavior, and mushroom body defects in a Drosophila model of fragile X syndrome." *Neuron* 45(5): 753-64.

Pieretti, M., F. P. Zhang, et al. (1991). "Absence of expression of the FMR-1 gene in fragile X syndrome." *Cell* 66(4): 817-22.

Reilly, M. T., I. A. Lobo, et al. (2008). "Effects of acamprosate on neuronal receptors and ion channels expressed in *Xenopus* oocytes." *Alcohol Clin Exp Res* 32(2): 188-96.

Rogers, S. J., D. E. Wehner, et al. (2001). "The behavioral phenotype in fragile X: symptoms of autism in very young children with fragile X syndrome, idiopathic autism, and other developmental disorders." *J Dev Behav Pediatr* 22(6): 409-17.

Ronesi, J. A. and K. M. Huber (2008). "Metabotropic glutamate receptors and fragile x mental retardation protein: partners in translational regulation at the synapse." *Sci Signal* 1(5): pe6.

Tucker, B., R. I. Richards, et al. (2006). "Contribution of mGluR and Fmr 1 functional pathways to neurite morphogenesis, craniofacial development and fragile X syndrome." *Hum Mol Genet.* 15(23): 3446-58.

Yan, Q. J., M. Rammal, et al. (2005). "Suppression of two major Fragile X Syndrome mouse model phenotypes by the mGluR5 antagonist MPEP." *Neuropharmacology* 49(7): 1053-66.

While the novel technology has been illustrated and described in detail in the figures and foregoing description, the same is to be considered as illustrative and not restrictive in character, it being understood that only the preferred embodiments have been shown and described and that al changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

What is claimed is:

1. A method of treating a subject having an autism spectrum disorder, comprising the step of administering to the subject a composition that includes at least one homotaurine analog, wherein the homotaurine analog is at least one member selected from the group consisting of an acetylaminopropane sulfonate and an acetylaminopropane sulfonate salt, wherein the homotaurine analog is administered to the subject at a dose of at least one member selected from the group consisting of about a 333 mg dose, about a 666 mg dose, about a 999 mg dose, about a 1332 mg dose, about a 1665 mg dose, about a 1998 mg dose, about a 2331 mg dose, about a 2664 mg dose and about a 2997 mg dose.

2. The method of claim 1, wherein the homotaurine analog decreases neuronal glutamatergic signaling.

3. The method of claim 1, wherein the autism spectrum disorder includes Asperger's syndrome.

4. The method of claim 1, wherein the autism spectrum disorder includes an idiopathic autism.

5. The method of claim 1, wherein the autism spectrum disorder includes a pervasive developmental disorder not otherwise specified.

6. The method of claim 1, wherein the subject further has fragile X syndrome.

7. The method of claim 1, wherein the acetylaminopropane sulfonate salt includes a calcium acetylaminopropane sulfonate represented by Formula I:

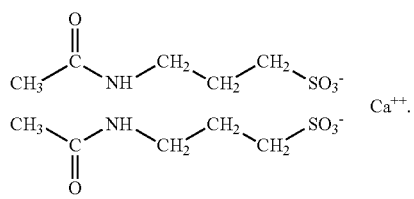

8. The method of claim 1, wherein the dose is about the 333 mg dose.

9. The method of claim 1, wherein the dose is about the 666 mg dose.

10. The method of claim 1, wherein the dose is administered daily to the subject in a single dose.

11. The method of claim 1, wherein the dose is administered daily to the subject in multiple doses.

12. The method of claim 11, wherein the multiple doses are three doses.

13. The method of claim 1, wherein the subject is a human.

14. A method of treating a subject having fragile X syndrome, comprising the step of administering to the subject a composition that includes at least one homotaurine analog, wherein the homotaurine analog is at least one member selected from the group consisting of an acetylaminopropane sulfonate and an acetylaminopropane sulfonate salt, wherein the homotaurine analog is administered to the subject at a dose of at least one member selected from the group consisting of about a 333 mg dose, about a 666 mg dose, about a 999 mg dose, about a 1332 mg dose, about a 1665 mg dose, about a 1998 mg dose, about a 2331 mg dose, about a 2664 mg dose and about a 2997 mg dose.

15. The method of claim 14, wherein the homotaurine analog decreases neuronal glutamatergic signaling.

16. The method of claim 14, wherein the subject further has an autism spectrum disorder.

17. The method of claim 14, wherein the acetylaminopropane sulfonate salt includes a calcium acetylaminopropane sulfonate represented by Formula I:

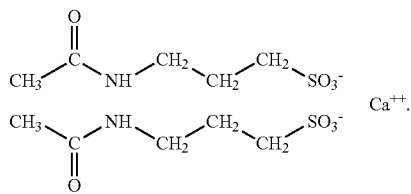

18. The method of claim 14, wherein the dose is about the 333 mg dose.

19. The method of claim 14, wherein the dose is about the 666 mg dose.

20. The method of claim 14, wherein the dose is administered daily to the subject in a single dose.

21. The method of claim 14, wherein the dose is administered daily to the subject in multiple doses.

22. The method of claim 21, wherein the multiple doses are three doses.

23. The method of claim 14, wherein the subject is a human.

24. A method of treating a human having fragile X syndrome, comprising the step of administering to the human a composition that includes Formula I:

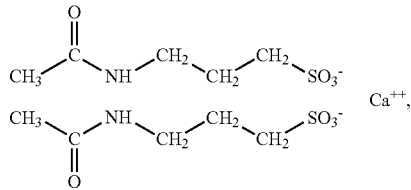

wherein the composition is administered to the subject in a dose of about 333 mg at a frequency of at least one member selected from the group consisting of two times a day and three times a day.

25. The method of claim 24, wherein the human further has an autism spectrum disorder.

26. A method of treating a human having an autism spectrum disorder, comprising the step of administering to the human a composition that includes Formula I:

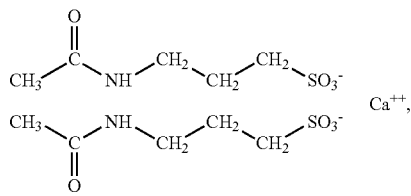

wherein the composition is administered to the subject in a dose of about 333 mg at a frequency of at least one member selected from the group consisting of two times a day and three times a day.

27. The method of claim 26, wherein the human further has fragile X syndrome.

* * * * *